United States Patent [19]
Wheeler

[11] Patent Number: 5,781,271
[45] Date of Patent: Jul. 14, 1998

[54] PORTABLE SAFETY SIDESHIELDS FOR EYE GLASSES

[75] Inventor: Richard R. Wheeler, Katy, Tex.

[73] Assignee: Richard Randolph Wheeler, Katy, Tex.

[21] Appl. No.: 790,027

[22] Filed: Jan. 28, 1997

[51] Int. Cl.⁶ ................................................... G02C 5/14
[52] U.S. Cl. .................................................. 351/121; 2/13
[58] Field of Search ................................ 351/121, 111, 351/41; 2/12, 13, 431

[56] References Cited

U.S. PATENT DOCUMENTS 5,397,567  3/1995  Vatterott ............................ 2/13
5,608,469  3/1997  Bollé ................................ 351/121

Primary Examiner—Hung X. Dang
Attorney, Agent, or Firm—Gerald E. Lester

[57] ABSTRACT

Low cost and portable safety side shields for safety eye glasses which substantially protect eyes from harm caused by projectiles impacting the eye through open areas between the wearer's head and the eye glass frames. The side shields have no conducting parts, are resistant to impact, shattering, and chemical corrosion, and are securely fastened to the ear pieces of the eye glasses by a stretchable tube. The side shields fit inside of the ear pieces without touching the eye glass wearers face, and overlap portions of the top, side and front of the lens frames to prevent latitudinal, longitudinal and rotational slippage that would expose the eyes. An alternative embodiment provides further eye protection by partially overlapping the front of the lens frames in the area of the eye glass hinges.

14 Claims, 5 Drawing Sheets

PORTABLE SAFETY SIDESHIELDS FOR EYE GLASSES

FIELD OF THE INVENTION

The invention relates generally to safety glasses, and more specifically to portable safety sideshields which fit on prescription and non-prescription safety glasses to prevent harm from projectiles which otherwise could enter the space between the safety glass lenses and the eyes of the wearer.

BACKGROUND OF THE INVENTION

In prior years, workers in environments that could be hazardous to the eyes were required to wear safety goggles which covered the face about the eyes, and which were cumbersome to the wearer to the point of being a distraction from the work to be done. The goggles further created vision aberrations that made the workers' task even harder, particularly when the goggles were fitted over prescription glasses or the wearer had contact lenses.

In view of the above, a migration toward the use of hardened prescription lenses for safety glasses occurred. The purchase of such prescription safety glasses, however, has proved too expensive for the wearer who in addition must purchase a separate pair of prescription eye glasses for regular daily wear. A perceived need to make prescription safety glasses acceptable both for use in hazardous areas, and for casual wear, gave rise to the introduction of safety side shields. The safety side shields may be added to eye glasses with hardened prescription lenses for a less obtrusive fit to the wearer than the old style safety goggles.

Safety side shields for prescription glasses are known which are permanently fixed with metal brads, or are permanently molded as an integral part of ear pieces and eye glass frames. While providing a more comfortable fit for work in hazardous areas, such glasses are too bizarre in appearance for casual wear. For regular daily wear, therefore, the user must purchase a second pair of prescription glasses.

It has become obvious that to gain wider acceptance of the use of eye glasses, portable safety side shields need to be provided which may easily be mounted and detached from the eye glass frames. A wearer then may mount the side shields on eye glass frames when in a hazardous environment, and remove the side shields for casual every day wear.

Portable safety sideshields are known which partially overlap the side, front, and top of the lens frames, and which employ either metal fasteners or elastic bands with metal tips to attach to the ear pieces of the eye glass frames. The side shields are difficult to mount to the eye glass frames, and the protection provided by such side shields is easily lost through slight inadvertent impact or rotational movement of the shields. Further, such shields provide no protection from projectiles moving diagonally across the face at the rear of a lens, and because of their conducting parts create an electrical hazard when working in environments with high current electrical fields. In addition, the conducting parts are susceptible to chemical corrosion, and upon deterioration may come apart during impact to injure the eye.

Many of the known safety side shields have a hinge window to accommodate a wide range of eye glass hinge sizes. Such hinge windows, however, will allow projectiles moving in a primarily horizontal direction to impact the eye.

The portable safety side shields of the present invention are easily mounted to the eye glass frames, have no conductive parts, and have no component parts which upon deterioration by chemical corrosion or otherwise would cause personal injury. The safety side shields are secured to the ear pieces of the eye glass frames with a non-corrosive and stretchable tube, which interacts with areas of the side shield partially overlapping the top, side and front of the eye glass frames about the lens to resist rotational, longitudinal and latitudinal movement with respect to the eye glass frames. In an alternative embodiment, a fold over area of the safety side shields is added to partially overlap the front of the eye lens about the eye glass hinge to provide additional protection from projectiles moving in a primarily horizontal direction. Low cost production of the safety side shields has been contemplated in the design of the shields by accommodating the manufacture of all parts, except the stretchable tubes, from a same piece of material through use of a single die.

SUMMARY OF THE INVENTION

The present invention is directed to low cost, portable safety side shields for eye glasses which are easily mounted to eye glass frames, which have no conductive parts, and which have no parts susceptible to chemical corrosion. The safety side shields are fastened to the ear pieces of the eye glass frames with a non-corrosive and stretchable tube, which interacts with areas of the safety side shields that partially overlap the side, front and top of the eye glass frames about the lens to resist rotational, longitudinal and latitudinal movement with respect to the eye glass frames.

In one aspect of the invention, the safety sideshields partially overlap the top of the lens frames to protect against projectiles moving from top downward or diagonally across the face.

In another aspect of the invention, the safety sideshields have hinge covers protecting against projectiles entering the hinge window from the side.

In a further aspect of the invention, the safety side shields and their fastening means are flexibly resistant to impact and to disintegration upon impact.

In an alternative embodiment of the invention, a fold-over area is integrally added to the safety side shields to partially overlap the front of the eye glass frames, about the area of the eye glass hinges, to provide further protection from projectiles moving in a direction to enter a window created by the curvature of the eye glass frames, and the upper flap portion and the hinge cover of the side shields.

In a still further aspect of the invention, low cost production of the safety side shields is maintained by a design which accommodates the manufacture of all parts of the shields except the stretchable tubes from a same piece of non-corrosive, non-conducting, flexible, non-shattering, and transparent material through use of a single die.

DESCRIPTION OF PREFERRED EMBODIMENTS

In the description of the preferred embodiment which follows, same components and features are referred to by same reference numbers in the description of the drawings.

Figure 1:
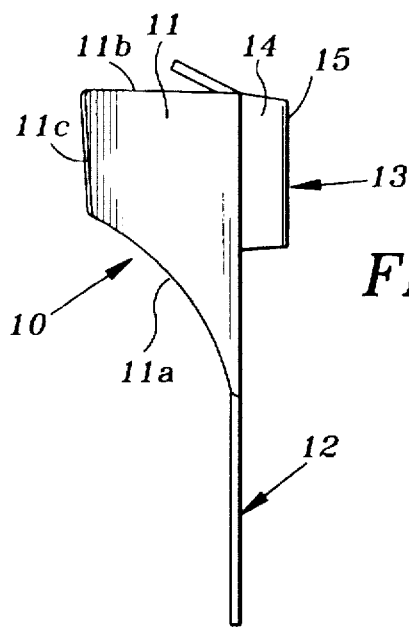
FIG. 1 is a planar view from the top of a right safety side shield in accordance with the present invention.

Referring to FIG. 1, a 0.040±0.002 inch thick unitary safety side shield 10 has an upper flap portion 11 folded at an oblique 67 degree angle from a plane parallel to a side surface 12. A rectangular, downward extending hinge cover 13 is formed by making an L-shaped cut 13a in the side surface 12, bending a first section 14 of the hinge cover 45 degrees from the plane of side surface 12, and bending a second section 15 of the hinge cover to become parallel with the plane of the side surface 12. The angle of bending of the section 15 may be varied to accommodate eye glasses from different manufacturers.

The L-shaped cut 13a forming the hinge cover 13 is 0.60 inches downward and 0.50 inches across. The section 14 is 0.15 inches long and 0.32 inches wide, and the section 15 is 0.61 inches long and 0.47 inches wide. The curved edge 11a of portion 11 is a 1.72 inch segment of a circle having a 3.0 inch radius. The edge 11b of flap portion 11 is 0.64 inches long, and the edge 11c is 0.55 inches long.

The safety side shield 10 is preferably formed from a clear plastic material which may be purchased commercially from a number of manufacturers. For example, the product PETG offered by Rexam Corporation of Oshkosh, Wis.; the product Lexan, order number 9034-112, offered by the General Electric Corporation of Mount Vernon, Ind.; and the product Acetate offered by Comco Graphics of Cherry Valley, Mass.

Figure 2:
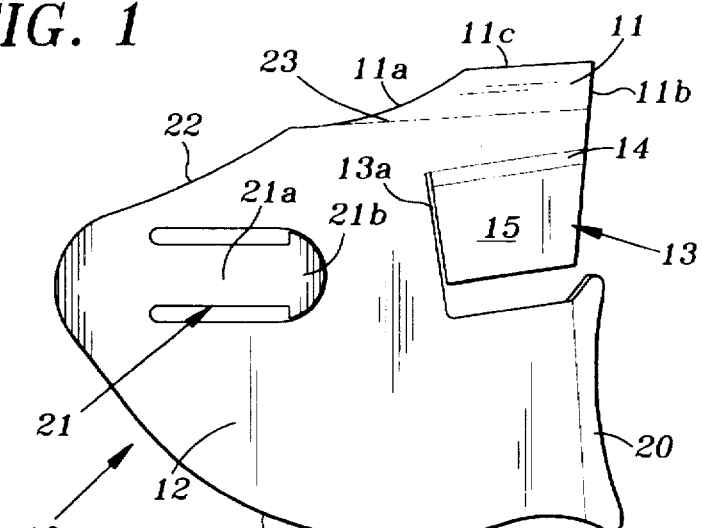
FIG. 2 is a side view of the outer surface of the right safety side shield of FIG. 1.

FIG. 2 is a side view of the outer surface of the safety side shield 10 of FIG. 1 showing the L-shaped cut 13a in the side surface 12 and the hinge cover 13 with sections 14 and 15. Also shown is a forward flap portion 20 of side surface 12 which is folded inward 90° degrees from the plane of side surface 12.

An arrow shaped arm 21 also is cut from the side surface 12, and is a part of the fastening means that is used to secure the safety side shield to an ear piece of the eye glass frames. The shaft 21a of the arrow shaped arm 21 is preferably 0.250 inches wide, with the arrow head being of a size to allow a stretchable tube to fit over the arrow head and snugly about the shaft.

When the safety side shield 10 is secured to an eye glass frame by threading an eye glass ear piece underneath the hinge cover 13 along the side surface 12, and through a stretchable tube that is about the arrow shaped arm 21, the flap portion 11 will partially overlap the top surface of the lens frame, and the flap portion 20 will partially overlap the front surface of the lens frame and lens. Further, the hinge of the ear piece of the eye glasses will be positioned beneath the hinge cover 13. The safety side shield so fitted is highly resistant to any rotational movement about the ear piece, and to any latitudinal or longitudinal movement along the ear piece. Further, the window created by the L-shaped cut 13a is covered by the hinge cover 13 to provide protection against projectiles entering the window to injure the eye. The side surface 12, and arrow shaped arm 21 act in concert to further shield the eye from projectiles.

The arrow shaped arm 21 is angled downward 8 degrees from the upper fold line of the section 14 to cause the bottom of the L-shaped cut 13a to impinge upon the bottom of the eye glass hinge to better cover the area around the hinge.

The side surface 12 has an edge 22 which is sloped downward 45 degrees from a fold crease 23, and which subtends in an arced edge 24 of safety side shield 10 which is a 1.60 inch segment of a circle having a radius of 1.38 inches.

Figure 3:
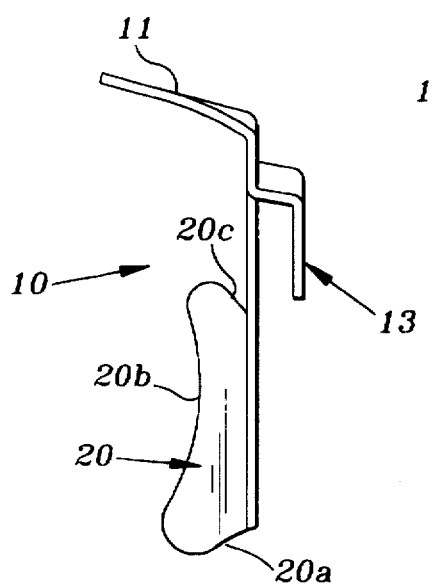
FIG. 3 is a rear view of the right safety side shield of FIG. 1.

Referring to FIG. 3, the safety shield as viewed from the rear is shown with flap portions 11 and 20, and hinge cover 13. The flap portion 20 has three curved edges 20a, 20b, and 20c. The edge 20a is curved outward in a convex arc which is a 0.47 inch sector of a circle having a radius of 0.50 inches. Further, the curved edge 20b is concave outward, and is a 0.23 inch sector of a circle having a radius of 0.13 inches. The curved edge 20c is convex outward and is a 0.94 inch sector of a circle having a radius of 1.0 inches.

Figure 4:
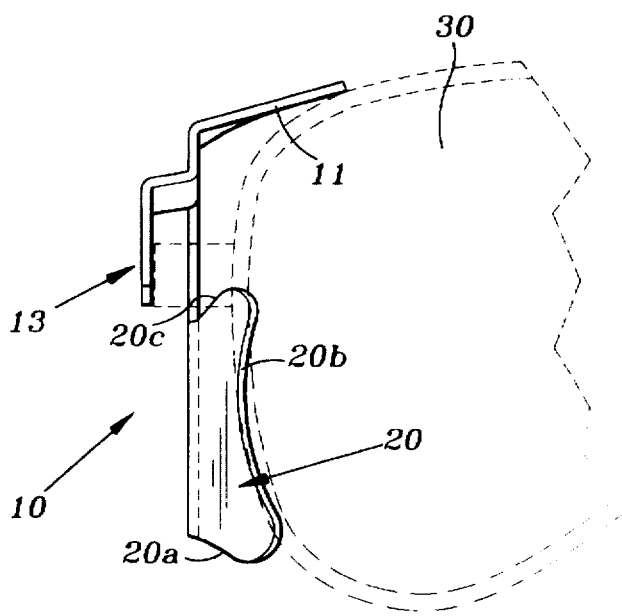
FIG. 4 is a front view of the right safety shield of FIG. 1.

FIG. 4 illustrates the safety side shield 10 from the front, as will be observed by a party looking into the face of an eye glass wearer who is using the safety shields in accordance with the invention. The dotted outline 30 depicts a lens as it will fit beneath the flap portion 11 and behind the flap portion 20.

Figure 5:
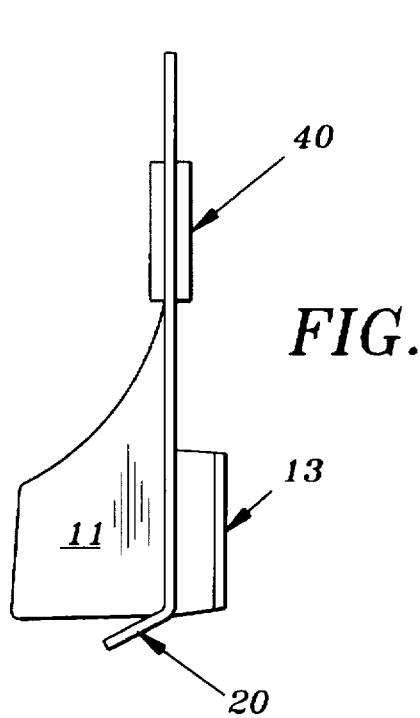
FIG. 5 is a planar view looking upward from the bottom of the right safety side shield of FIG. 1.

FIG. 5 is a view from the bottom of the safety side shield 10 showing the flap portion 20, hinge cover 13, flap portion 11, and a stretchable tube 40 which is fitted about the arrow shaped arm 21 of FIG. 2.

The tube 40 may be any resilient, flexible material which is resistant to impact and chemical corrosion, and which is non-conductive. By way of example, a silicon tubing offered by Norton Performance Plastics as a peroxide cured SPX-40 product with 3/16 inch inner diameter, 5/16 inch outer diameter, and 1/16 inch thick walls may be used.

Figure 6:
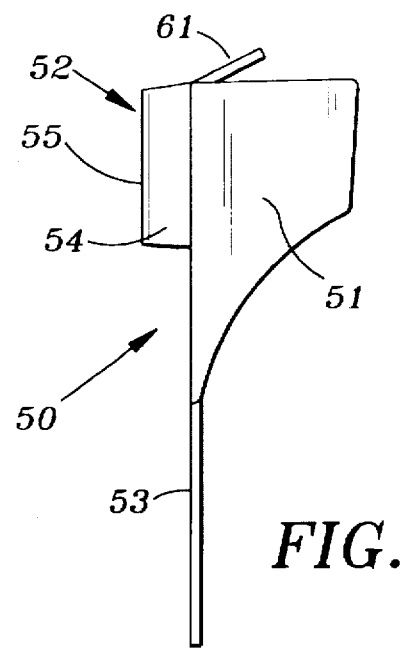
FIG. 6 is a planar view from the top of a left safety side shield in accordance with the present invention.

A top view of the left safety side shield 50 is shown in FIG. 6, with a flap portion 51 folded 67 degrees from vertical, and a downward extending hinge cover 52 which is formed by making an L-shaped cut in the side surface 53 of the shield. The hinge cover 52 is comprised of a first section 54 which is 45 degrees from vertical, and a second section 55 which in the Figure is shown parallel to the plane of the side surface but which may vary in angle from the section 54 to accommodate a wide variety of eye glass frames.

Figure 7:
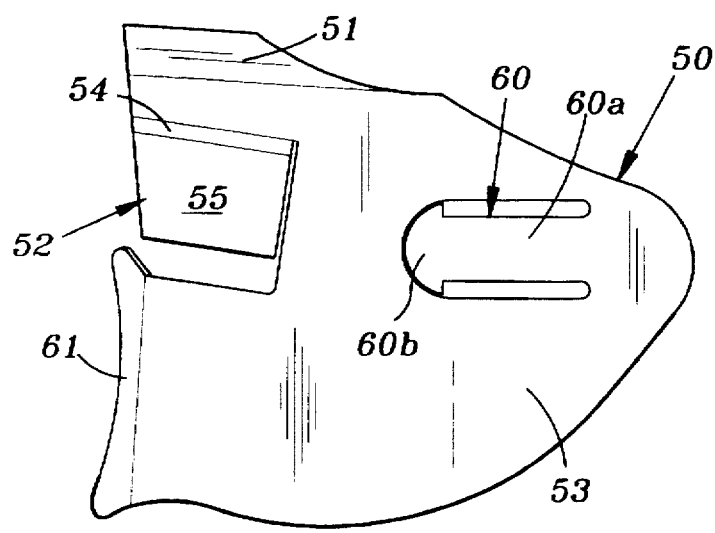
FIG. 7 is a side view of the outer surface of the left safety shield of FIG. 6.

The outer surface of the left safety side shield 50 is shown in FIG. 7, with an arrow shaped arm 60 having a shaft arm 60a and an arrow head 60b being cut out of the side surface 53. A flap portion 61 of the safety side shield 50 is folded inward 90° degrees from the plane of the side surface 53.

Figure 8:
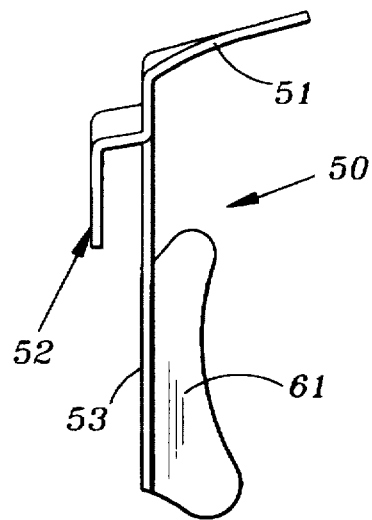
FIG. 8 is a rear view of the left safety shield of FIG. 6.
Figure 9:
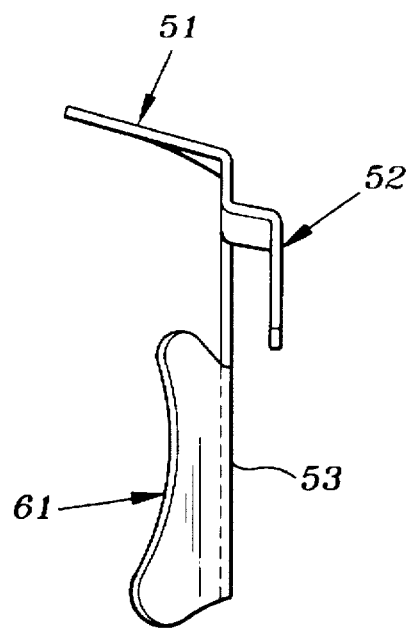
FIG. 9 is a front view of the left safety shield of FIG. 6.

A rear view of the safety side shield 50 is illustrated in FIG. 8, with the flap portion 51, hinge cover 52 and flap portion 61 being in view. The front view of the safety shield 50 is shown in FIG. 9, with the flap portion 51, hinge cover 52, flap portion 61, and side surface 53 again being shown.

Figure 10:
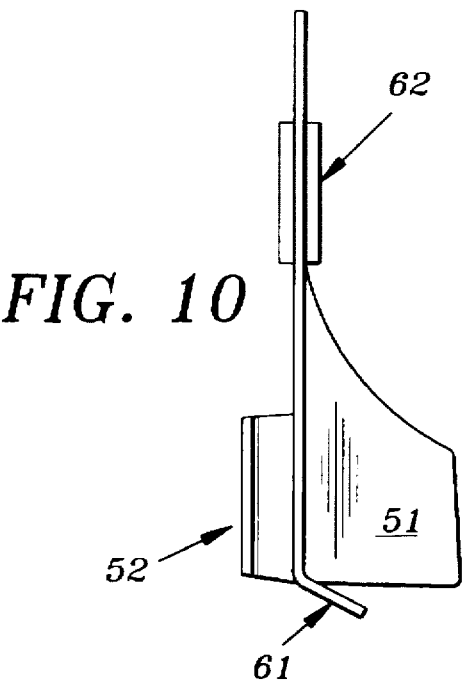
FIG. 10 is a view looking upward at the bottom of the left safety side shield of FIG. 6.

FIG. 10 shows a view from the bottom of the safety side shield 50 with flap portion 51, hinge cover 52, and flap portion 61. A tube 62 is slipped over the arrow head 60b to fit snugly about the shaft arm 60a of arrow shaped arm 60, as further illustrated in FIG. 7.

As the right safety side shield illustrated in FIGS. 1-5 is a mirror image of the left safety side shield illustrated in FIGS. 6-10, the dimensions of the left safety side shield will not be further described.

Figure 11:
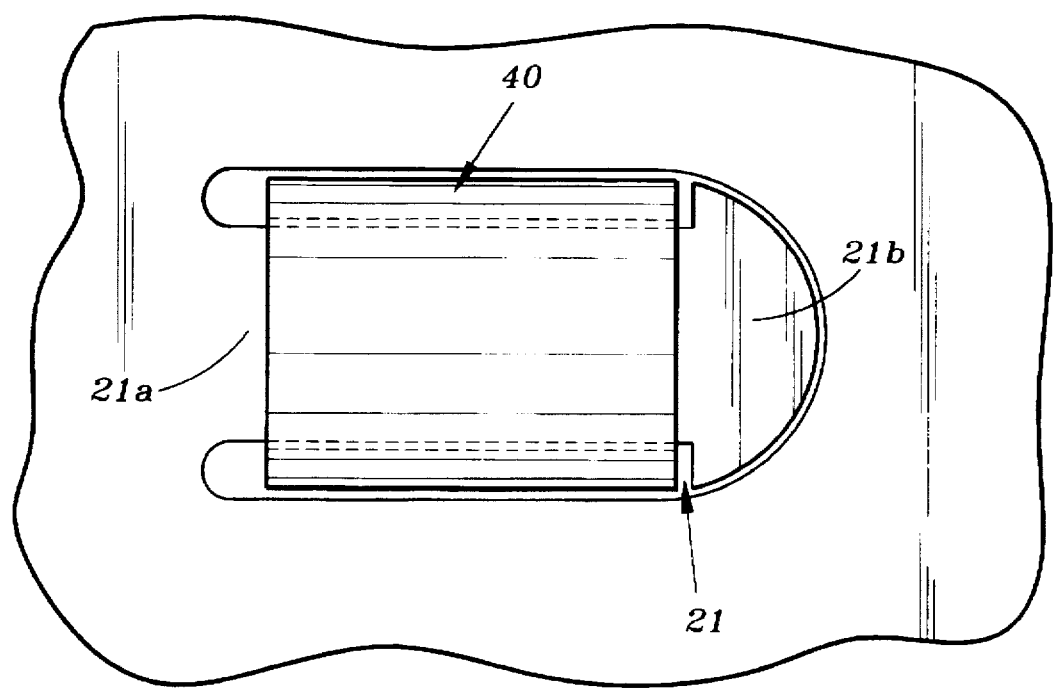
FIG. 11 is a side view of the fastening means used by the safety shields of FIGS. 1 and 6.

FIG. 11 depicts the arrow shaped arm 21 of FIG. 2 in more detail. The head 21b of the arm 21 may be bent out from the side surface 12, and the tube 40 slipped over the head to fit snugly around the shaft 21a. When an eye glass ear piece is inserted between the outer surface of the arm 21 and the tube 40, the restriction in movement provided by the tube 40 acts in concert with flap portions 11 and 20 to prevent latitudinal, longitudinal, and rotational movement of the side shield 10 with respect to the eye glasses.

Figure 12:
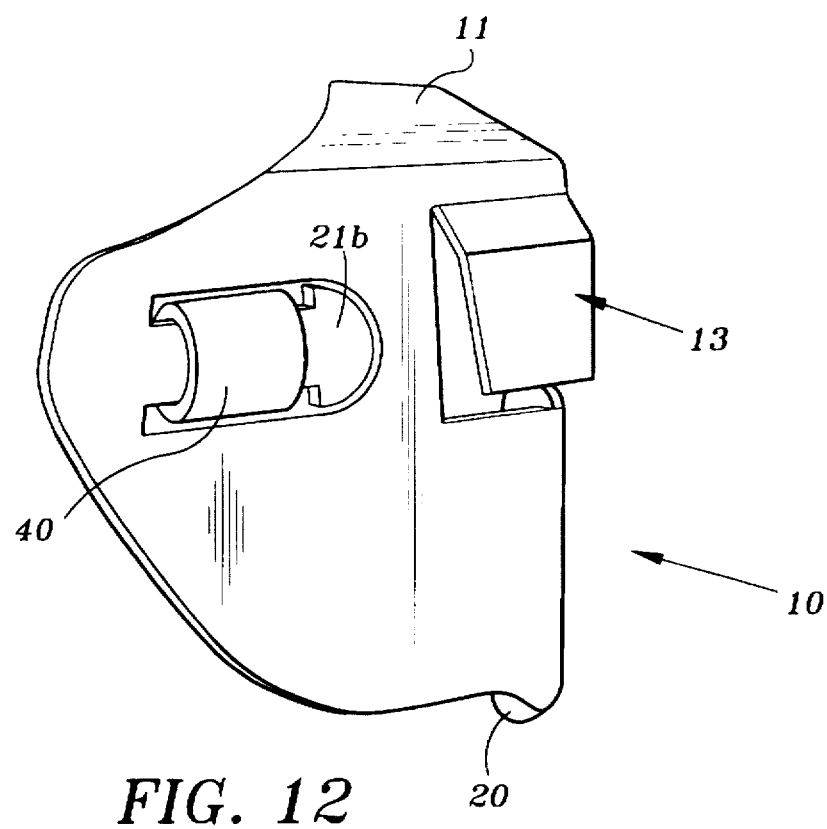
FIG. 12 is a perspective view of the outer surface of the right safety shield of FIG. 1.
Figure 13:
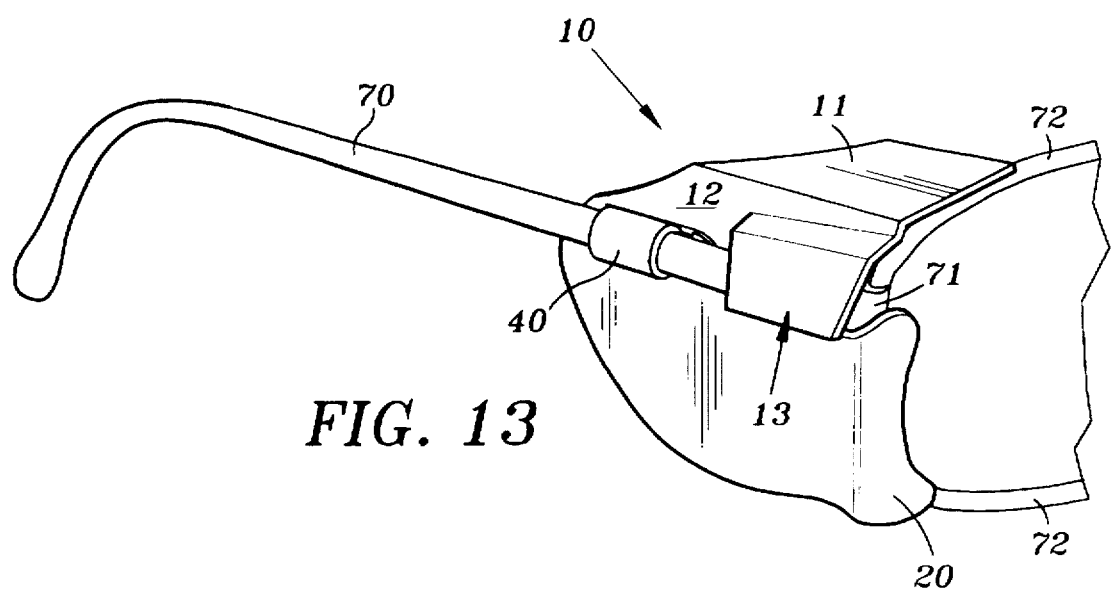
FIG. 13 is a perspective view of the right safety side shield of FIG. 1 attached to an ear piece of a pair of eye glasses.

The stability provided by the safety side shield is made more apparent in FIG. 12. When the right side ear piece of a pair of eye glasses is slipped under the hinge cover 13 and slipped through the tube 40 between the tube and the arrow shaped arm 21, a top portion of the lens frame of the eye glasses will come into contact with the flap portion 11. In addition, the flap portion 20 will come in contact with the front face of the right side lens. The resulting combination is shown in FIG. 13, where the safety side shield 10 of FIG. 12 is fitted onto a pair of eyeglasses in accordance with the invention. An ear piece 70 has been slipped through the tube 40 to be located between the tube and the arrow shaped arm 21 (not shown). An eyeglass hinge 71 is shown as being located under the hinge cover 13, and an eye glass lens 72 is located under the flap portion 11 and behind the flap portion 20. In this position, the eye glasses will be prevented from rotational, lateral, and longitudinal movement relative to the safety side shield 10, and the eye is protected from projectiles moving in a primarily horizontal or a more vertical than horizontal direction.

Figure 14:
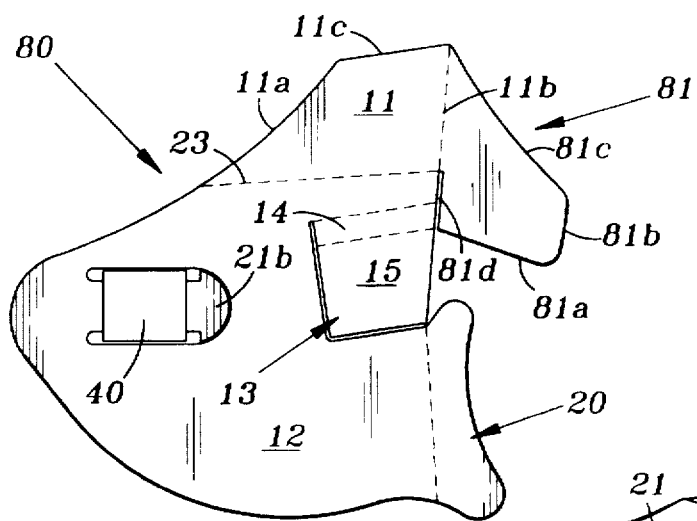
FIG. 14 is a planar view of a template for a right safety side shield lying flat without areas being folded for mounting to eye glass frames.

An alternative embodiment of the invention is shown in FIGS. 14 through 17. FIG. 14 depicts a safety side shield 80 with side surface 12, flap portions 11 and 20, and hinge cover 13 with sections 14 and 15 as before described. Further, a fastening means with an arrow shaped arm 21, and a stretchable tube 40, is shown as before described. In addition, a flap portion 81 with edges 81a, 81b, and 81c, and with an edge 81d that is an extension of edge 11b is shown. The edge 81a is 0.63 inches long, edge 81b is 0.25 inches long, and edge 81c is a segment of a convex outward curve having a radius of curvature of 3.00 inches. The edge 81d is 0.29 inches long.

Figure 15:
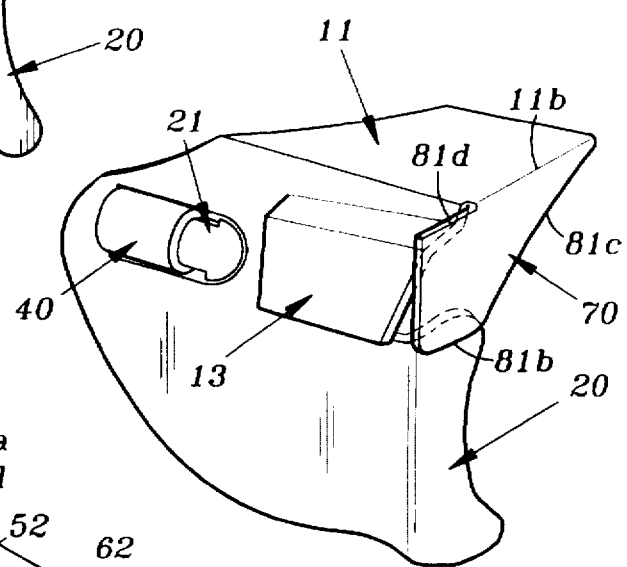
FIG. 15 is a perspective view of the right safety side shield of FIG. 14 with areas folded for mounting to eye glass frames.

FIG. 15 shows a right safety side shield 80 with tube 40 fitted over arrow head 21b, and with flap portions folded for mounting on eye glass frames. Forward flap portion 81 is folded downward along edges 11b and 81d to partially cover a top portion of the forward flap portion 20. Foreign objects that otherwise could enter a window formed by the curvature of the eye glass frame, the upper flap portion 11, and the hinge cover 13 will be blocked from entering the space between a user's face and the eye glass frame.

Figure 16:
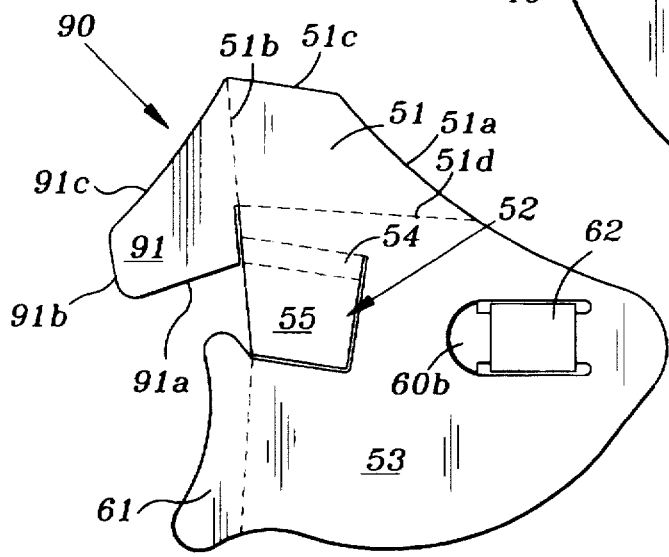
FIG. 16 is a planar view of a template for a left safety side shield lying flat without areas being folded for mounting to eye glass frames.

FIG. 16 depicts a left safety side shield 90 with side surface 53, a hinge cover 52 with sections 54 and 55, a fastening means with an arrow shaped arm 60, and flap portions 51 and 61 as before described. In addition, a flap portion 91 is shown with edges 91a, 91b, 91c, and 91d. As the template of FIG. 16 is a mirror image of the template of FIG. 14, the dimensions of FIG. 16 will not be further discussed.

Figure 17:
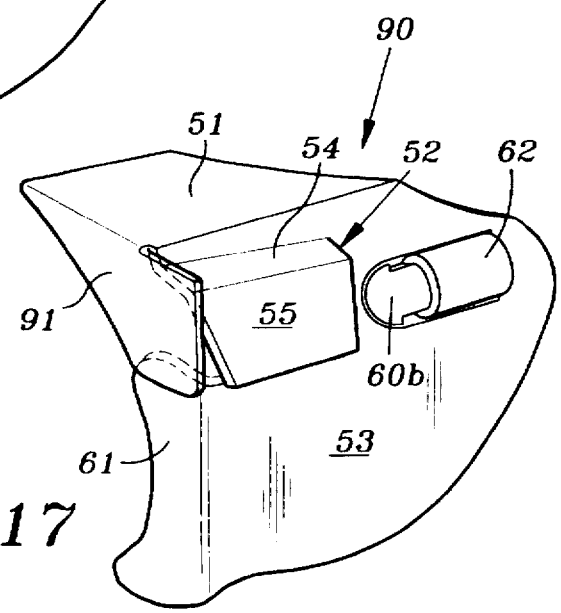
FIG. 17 is a perspective view of the left safety shield of FIG. 16 with areas folded for mounting to eye glass frames.

FIG. 17 shows the template 90 with tube 62 fitted over arrow head 60b, and with flap portions 51, 61, and 91 folded for mounting on eye glass frames. Again, with the flap portion 91 overlapping a top, forward surface of the flap portion 61, foreign objects that otherwise could enter a window formed by the curvature of the eye glass frame, the upper flap portion 51, and the hinge cover 52 are blocked from entry into the space between a user's face and the eye glass frames.

Portable and easy to mount safety side shields for eye glasses have been disclosed which are formed from non-conductive, non-corrosive, flexible, non-shattering and transparent material, and which include a fastening means comprised of an arrow shaped arm that allows the attachment of the side shields to ear pieces of eye glasses with a stretchable tube. The fastening means further operates in concert with upper and forward flap portions of the side shields to resist rotational, longitudinal, and latitudinal movement of the side shields with respect to the eye glass frame and ear pieces. In order to maintain low production costs, the safety side shields have been designed to allow all components except the stretchable tubes to be stamped from a single piece of material by using a single die.

It will be apparent to those of ordinary skill in the design and manufacture of safety glasses, that the shape and dimensions of the safety side shield parts disclosed herein may be revised, and that one or more parts of the safety side shields may be formed from different materials, or separately manufactured, and attached to the safety side shields without departing from the spirit of the claims which follow.

What is claimed is:

1. A portable safety side shield for safety glasses having portability among glasses of different types, sizes, and shapes, and having an eye glass frame for lenses, an ear piece, and a hinge for connecting said ear piece to said eye glass frame, which comprises:

an upper flap portion folded inward to cover an upper surface of said eye glass frame;

a forward flap portion folded inward to partially cover a front portion of said eye glass frame;

a hinge cover for overlapping said hinge;

a fastening arm for securing said portable safety side shield to said ear piece; and a side surface portion connected to said upper flap portion, said forward flap portion, said hinge cover and said fastening arm to form a barrier against foreign objects.

2. The portable safety side shield of claim 1, wherein said portable safety side shield is made of a non-conductive, non-corrosive, flexible, non-shattering, and transparent material.

3. The portable safety side shield of claim 1, wherein said upper flap portion is folded inward an acute angle from a plane of said side surface portion.

4. The portable safety side shield of claim 1, wherein said forward flap portion is folded inward ninety degrees from a plane of said side surface portion.

5. The portable safety side shield of claim 1 further having a second forward flap portion connected to said upper flap portion and partially overlapping a front surface of said forward flap portion to provide further protection against foreign objects.

6. Safety glasses having a pair of lenses seated within an eye glass frame, a pair of ear pieces, and a pair of transparent ear piece hinges connecting said pair of ear pieces to said eye glass frame, which comprises:

- a pair of transparent side shields, each having an upper flap portion folded inward to cover an upper surface of said eye glass frame, a forward flap portion folded inward to partially cover a front portion of said eye glass frame, a an outward extending hinge cover for overlapping one of said pair of eye glass hinges, and a fastening arm extending within a cut-out portion of each of said pair of side shields; and
- a pair of stretchable tubes, each wrapped around said fastening arm of one of said pair of side shields and one of said pair of ear pieces to secure said pair of side shields to said pair of ear pieces and position said pair of ear piece hinges beneath said hinge cover of said pair of side shields.

7. The safety glasses of claim 6, wherein said hinge cover for each of said pair of side shields is formed from an L-shaped cut in each of said pair of side shields, and said fastening arm is inclined downward with respect to said hinge cover to force a bottom boundary of said L-shaped cut against an underside of each of said pair of eye glass hinges.

8. The safety glasses of claim 6, wherein said fastening arm for each of said pair of side shields is arrow shaped, and said pair of tubes is stretchable to fit over an arrow head onto a shaft of said fastening arm.

9. The safety glasses of claim 6, wherein said pair of side shields each have a second forward flap portion connected to said upper flap portion to partially overlap a front surface of said forward flap portion to provide further protection against foreign objects.

10. Portable safety side shields for eye glasses having portability among glasses of different types, sizes and shapes, and having lenses seated within an eye glass frame, ear pieces, and ear piece hinges for connecting said ear pieces to said eye glass frame, each of said portable safety side shields comprising:

- fastening means for securing said portable safety side shields to said ear pieces, and in working relationship with said portable safety side shields for restricting relative latitudinal, longitudinal, and rotational movement between said eye glasses and said portable safety side shields;
- hinge cover means for accommodating a range of eye glass hinge sizes while blocking paths of foreign objects;
- an upper flap portion overlapping a top portion of said eye glass frame to protect against downward traveling foreign objects and inhibiting rotational movement of said portable safety side shields with respect to said ear pieces;
- a first forward flap portion overlapping a front surface of said eye glass frame to inhibit longitudinal movement of said portable safety side shields relative to said eye glass frame; and
- a side surface portion connected to said fastening means, said hinge cover means, said upper flap portion, and said first forward flap portion.

11. The portable safety side shields of claim 10, further including a second forward flap portion connected to said upper flap portion and partially overlapping a front surface of said first forward flap portion to further protect against foreign objects.

12. The portable safety side shields of claim 10, wherein said fastening means is comprised of an arrow shaped arm, and said arrow shaped arm, said hinge cover means, said upper flap portion, said first forward flap portion, and said side surface portion are formed as integral connected parts of a same piece of non-conducting, non-corrosive, flexible, non-shattering and transparent piece of material.

13. Portable safety side shields for eye glasses having portability among glasses of different types, sizes and shapes, and having lenses seated within an eye glass frame, ear pieces, and ear piece hinges for connecting said ear pieces to said eye glass frame, each of said portable safety side shields comprising:

- fastening means for securing said portable safety side shields to said ear pieces, and in working relationship with said portable safety side shields for restricting relative latitudinal, longitudinal, and rotational movement between said eye glasses and said portable safety side shields;
- hinge cover means for accommodating a range of eye glass hinge sizes while blocking paths of foreign objects;
- an upper flap portion overlapping a top portion of said eye glass frame to protect against downward traveling foreign objects and inhibiting rotational movement of said portable safety side shields with respect to said ear pieces;
- a first forward flap portion overlapping a front surface of said eye glass frame to inhibit longitudinal movement of said portable safety side shields relative to said eye glass frame;
- a second forward flap portion connected to said upper flap portion and partially overlapping front surfaces of said eye glass frame and said first forward flap portion to provide further protection against foreign objects, and
- a side surface portion connected to said fastening means, said hinge cover means, said upper flap portion, and said first forward flap portion.

14. The portable safety side shields of claim 13, wherein said fastening means is comprised of an arrow shaped arm, and said fastening means, said hinge cover means, said upper flap portion, said first forward flap portion, said second forward flap portion, and said side surface portion are formed from a same piece of non-conductive, non-corrosive, flexible, non-shattering, and transparent material.

* * * * *